United States Patent
Xiao et al.

(10) Patent No.: US 11,576,942 B2
(45) Date of Patent: Feb. 14, 2023

(54) TRADITIONAL CHINESE MEDICINE COMPOSITION AND PREPARATION METHOD AND APPLICATION THEREOF

(71) Applicant: JIANGSU KANION PHARMACEUTICAL CO.,LTD., Jiangsu (CN)

(72) Inventors: Wei Xiao, Jiangsu (CN); Zhengkuan Wang, Jiangsu (CN); Ningbo Cheng, Jiangsu (CN); Zhenzhong Wang, Jiangsu (CN); Kejin Zhu, Jiangsu (CN)

(73) Assignee: JIANGSU KANION PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 17/271,487

(22) PCT Filed: Aug. 22, 2019

(86) PCT No.: PCT/CN2019/101869
§ 371 (c)(1),
(2) Date: Feb. 25, 2021

(87) PCT Pub. No.: WO2020/042988
PCT Pub. Date: Mar. 5, 2020

(65) Prior Publication Data
US 2021/0196778 A1    Jul. 1, 2021

(30) Foreign Application Priority Data
Aug. 30, 2018   (CN) .......................... 201811000257.1

(51) Int. Cl.
| | |
|---|---|
| *A61K 36/736* | (2006.01) |
| *A61K 47/69* | (2017.01) |
| *A61K 36/076* | (2006.01) |
| *A61K 36/54* | (2006.01) |
| *A61K 36/65* | (2006.01) |

(52) U.S. Cl.
CPC .......... *A61K 36/736* (2013.01); *A61K 36/076* (2013.01); *A61K 36/54* (2013.01); *A61K 36/65* (2013.01); *A61K 47/6951* (2017.08); *A61K 2236/15* (2013.01); *A61K 2236/331* (2013.01); *A61K 2236/333* (2013.01); *A61K 2236/51* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| | | | |
|---|---|---|---|
| 2002/0160059 A1 | 10/2002 | Xiao | |
| 2010/0183660 A1* | 7/2010 | Xiao | ................... A61K 36/076 424/195.15 |

FOREIGN PATENT DOCUMENTS

| | | |
|---|---|---|
| CN | 1748735 A | 3/2006 |
| CN | 101495129 A | 7/2009 |
| CN | 101653491 A | 2/2010 |
| CN | 104815025 A | 8/2015 |
| CN | 106153803 A | 11/2016 |
| CN | 107308234 A | 11/2017 |

OTHER PUBLICATIONS

Rong-Hua, et al., Chinese J. Nat. Med., 16:313. (Year: 2018).*
CN104815025A (English translation retrieved from Google Patents). (Year: 2015).*
Chinese Application No. 201811000257.1, First Office Action and Search Report dated Jan. 14, 2022, 15 pages.
Japanese Application No. 2021511597, Notice of Reasons for Refusal dated Mar. 22, 2022, 16 pages.
Tokyo Crude Drug Association "Composition of Chinese herbal medicine and its preparation method and application" Mar. 21, 2017, pp. 2-4.

* cited by examiner

*Primary Examiner* — Michael Barker
(74) *Attorney, Agent, or Firm* — MagStone Law, LLP; Enshan Hong

(57) ABSTRACT

A traditional Chinese medicine composition, made from cassia twig, *poria*, *Cortex moutan*, *Radix paeoniae* alba, peach kernel in equal proportions. The traditional Chinese medicine composition comprises paeoniflorin, amygdalin, benzoylpaeoniflorin, cinnamic acid, paeonol, and cinnamaldehyde. The composition has the advantages of high production efficiency, high content of effective ingredients, high transfer rate of *poria* acid, reduced hygroscopicity, and improved dissolution of index ingredients.

10 Claims, No Drawings

TRADITIONAL CHINESE MEDICINE COMPOSITION AND PREPARATION METHOD AND APPLICATION THEREOF

RELATED APPLICATIONS

This is a U.S. national stage of international application No. PCT/CN2019/101869 filed on Aug. 22, 2019, which claims priority to Chinese Patent Application No. 201811000257.1, filed with the China National Intellectual Property Administration (CNIPA) on Aug. 30, 2018, the entire content of which is incorporated herein by reference.

TECHNICAL FIELD

The present invention relates to a composition comprising traditional Chinese medicines *Ramulus cinnamomi* and *Poria cocos*, and a preparation method and application thereof.

BACKGROUND

The *Ramulus cinnamomi-Poria cocos* capsule is composed of five traditional Chinese medicines: *Ramulus cinnamomi, Poria cocos, Cortex moutan, Radix paeoniae* alba, and peach kernel. The *Ramulus cinnamomi-Poria cocos* capsule has the effects of promoting blood circulation, removing blood stasis, and eliminating symptoms, and mainly treats concretion lumps, amenorrhea, dysmenorrhea, and postpartum lochia of women caused by blood stasis and obstruction of the collaterals; uterine fibroids, chronic pelvic inflammatory mass, dysmenorrhea, endometriosis, and ovarian cysts with the above symptoms. The *Ramulus cinnamomi-Poria cocos* capsule can also be used for female breast cystic hyperplasia, which is a syndrome of blood stasis and collateral obstruction, with symptoms such as breast pain, breast lumps, sternal swelling and tightness; or for prostate hyperplasia, which is a syndrome of stasis and bladder, with symptoms such as uncomfortable urination and lower abdominal pain.

A method for preparing the *Ramulus cinnamomi-Poria cocos* capsule disclosed in the prior art mainly comprises the steps of steam distillation, ethanol extraction, concentration, granulation, drying, etc., from *Ramulus cinnamomi, Radix paeoniae* alba, *Poria cocos*, peach kernel, and *Cortex moutan* according to the required weight ratio. The defects of this method are as follows: the medicine prepared by this method has relatively low content of active ingredients, poor dissolution, low production efficiency, high noise, and high requirements for dust removal; therefore, it is necessary to improve the existing process methods to obtain APIs or preparations with high content of active ingredients.

SUMMARY OF THE INVENTION

In view of this, the present invention provides a method for preparing a composition comprising *Ramulus cinnamomi, Poria cocos, Cortex moutan, Radix paeoniae* alba, and peach kernel in equal proportions, wherein the method comprises the following steps:

(a) preparation of *Poria cocos* powder intermediate: taking a sufficient amount of *Poria cocos* powder, drying at 70° C. to a moisture content of ≤5.0%, pulverizing with a 120-mesh sieve, and taking 30-49% of the prescription amount of *Poria cocos* powder which is the *Poria cocos* powder intermediate, wherein preferably taking 45% of the prescription amount of *Poria cocos*;

(b) preparation of a paeonol inclusion compound: extracting paeonol from *Cortex moutan* by direct connection steam distillation, and collecting aromatic water and medicinal dregs for use later; resting the aromatic water for 48-72 hours until the paeonol aromatic water is completely crystallized, and filtering and drying in the shade to obtain paeonol crystals; including with β-cyclodextrin to prepare a paeonol inclusion compound;

(c) preparation of a *Ramulus cinnamomi* volatile oil inclusion compound: extracting the volatile oil from *Ramulus cinnamomi* by direct connection steam distillation, adding ethyl acetate extraction during the extracting process, and collecting aromatic water at the ethyl acetate layers and medicinal dregs for use later; placing the aromatic water layer in a separating funnel, resting the aromatic water layer, separating the upper ethyl acetate layer, extracting the lower layer with equal amount of ethyl acetate, combining the ethyl acetate layers, carrying out reduced-pressure recovery, and adding ethanol for further concentration to obtain pure volatile oil; including with β-cyclodextrin to prepare a *Ramulus cinnamomi* volatile oil inclusion compound;

(d) preparation of spray-dried powder intermediates of extracts: carrying out alcohol extraction and water extraction on *Cortex moutan* dregs, carrying out alcohol extraction and water extraction on *Ramulus cinnamomi* dregs, and carrying out alcohol extraction and water extraction on *Radix paeoniae* alba, peach kernel, and 51-70% of the prescription amount of *Poria cocos*; concentrating the above alcohol extracts or water extracts separately, combining the concentrated extracts for further concentration to obtain extract, and mixing after spray drying to obtain spray-dried powder; and (e) total mixing: mixing the *Poria cocos* powder intermediate, the spray-dried powder intermediates of extracts, the paeonol inclusion compound, and the *Ramulus cinnamomi* volatile oil inclusion compound, wherein the total mixing time is preferably ≥30 min.

Further, in step (a), after pulverizing part of *Poria cocos*, sieving the obtained powder with a sieve of 60-200 meshes, preferably with a 120-mesh sieve. The moisture content of the dried and sterilized *Poria cocos* is preferably less than 5%; the moisture difference of the sample before and after mixing is detected, and the moisture content is controlled at <5%.

Specifically, in step (b):

collecting aromatic water in about 4-6 folds, preferably in 5-fold amount, in the steam distillation process; specifically, putting the decoction pieces of *Cortex moutan* into an extraction tank, and extracting the paeonol by steam distillation and filtered with filter cloth, and controlling the flow rate of the aromatic waterto about 5 kg/min, collecting aromatic water in about 5-fold amount; preferably, the filter cloth is of 100 meshes;

In the step of resting and crystallization of the *Cortex moutan* aromatic water, the obtained paeonol aromatic water is allowed to rest until the paeonol aromatic water is completely crystallized, and filtering out the crystals and then drying the crystals in the shade in a purifying zone, thus obtaining paeonol crystals for use later; preferably, the filter cloth is of 200 meshes:

The inclusion with β-cyclodextrin specifically comprises: adding β-cyclodextrin to purified water in 2.7-fold amount of the β-cyclodextrin, stirring well, and heating to 60° C.; adding paeonol in an amount ⅙-1/12 of the addition of β-cyclodextrin to ethanol in 4-6 folds amount, and heating to dissolve the paeonol; pouring the hot paeonol solution into the β-cyclodextrin solution; processing the solution with a colloid mill for 30 minutes, discharging the solution, resting overnight for 16-24 hours, carrying out suction filtering, drying under normal pressure, pulverizing, and mixing for 15 minutes to obtain the paeonol inclusion compound; preferably, sieving the pulverized paeonol inclusion compound with a 100-mesh sieve, and the drying temperature is carried out at 50° C.

Further, in step (c),

The amount of ethyl acetate added in the steam distillation process is 3.5% (weight-volume ratio) of the amount of medicinal materials; specifically, putting the decoction pieces of *Ramulus cinnamomi* into an extraction tank, and subjecting steam distillation to extract volatile oil; in the extraction process, adding the amount of ethyl acetate which is 3.5% of the amount of the medicinal material for extraction, and collecting the aromatic water at the ethyl acetate layer; preferably, the extraction time is 5 hours;

In the refining step of *Ramulus cinnamomi* aromatic water, after resting the aromatic water at the ethyl acetate layer, separating the upper ethyl acetate layer, re-extracting the lower layer with the same amount of ethyl acetate, combining the ethyl acetate layers and then concentrating, and adding ethanol in the same amount as the crude volatile oil for re-concentration to obtain pure volatile oil for use later; preferably, the initial concentration temperature with ethyl acetate is 60° C., and the concentration with ethanol is carried out at 80° C.; preferably the final concentration temperature is 90° C. and the concentration time is 20 minutes.

Including with β-cyclodextrin specifically comprises: adding β-cyclodextrin to ethanol in 4-6 folds amount, preferably in 5-fold amount, stirring well to obtain a suspension, and adding the volatile oil in an amount ⅙-1/12, preferably 1/10, of the addition of β-cyclodextrin to the suspension, stirring well, processing the solution with a colloid mill for 30 minutes, discharging the solution, resting for 16-24 hours, and carrying out suction filtering, drying, pulverizing, and mixing for 15 minutes to obtain *Ramulus cinnamomi* volatile oil (cinnamon oil) inclusion compound; preferably, the ethanol is ethanol with a concentration of 20%, the pulverized inclusion compound is sieved with a 100-mesh sieve, and the drying is carried out at 50° C.

Preferably, in step (d),

The *Radix paeoniae* alba, the peach kernel, and the 51-70% of the prescription amount of *Poria cocos* are fed in an order of *Radix paeoniae* alba at the bottom, peach kernel in the middle, and *Poria cocos* at the top;

During the preparation process of the spray-dried powder, setting the inlet air temperature to 165-170° C., and controlling the outlet air temperature to 90-95° C. during the spray-drying process; cooling the resulting powder to room temperature, and then discharging and mixing to obtain the spray-dried powder.

Preferably, the above-mentioned preparation method includes a pre-processing for the medicinal materials used as follows:

Cutting the *Poria cocos* decoction pieces with a size of about 0.5-1 cm; washing the *Cortex moutan* and then making into decoction pieces; the rest of the medicinal materials can be pure decoction pieces for use.

The present invention provides a traditional Chinese medicine composition, comprising *Ramulus cinnamomi, Poria cocos, Cortex moutan, Radix paeoniae* alba, and peach kernel in equal proportions, wherein the traditional Chinese medicine composition also contains paeoniflorin, amygdalin, benzoylpaeoniflorin, cinnamic acid, paeonol, and cinnamic aldehyde.

Further, the content of paeoniflorin accounts for 15 mg/g or above of the traditional Chinese medicine composition, the content of amygdalin accounts for 10 mg/g or above of the traditional Chinese medicine composition, and the content of paeonol accounts for 10 mg/g or above of the traditional Chinese medicine composition.

Preferably, the transfer rate of *Poria* acid in the traditional Chinese medicine composition is greater than 90%.

The present invention provides a preparation method of a composition or preparation comprising *Ramulus cinnamomi* and *Poria cocos*, using the Chinese herbal medicine *Ramulus cinnamomi, Poria cocos, Cortex moutan, Radix paeoniae* alba, and peach kernel as raw materials, and the method includes the following steps:

(a) preparation of a *Poria cocos* powder intermediate;
(b) preparation of a paeonol (*Cortex moutan* extract) inclusion compound;
(c) preparing a *Ramulus cinnamomi* volatile oil (*Ramulus cinnamomi* extract) inclusion compound;
(d) preparation of spray-dried powder intermediate of extract;
(e) totally mixing; and
(f) granulating to obtain a product;

wherein, step (d) further includes the step of extracting *Radix paeoniae* alba, peach kernel and 55% of the prescription amount of *Poria cocos;* step (e) includes mixing the *Poria cocos* powder intermediate, the spray-dried powder intermediate, the paeonol inclusion compound, and the cinnamomi oil inclusion compound.

Preferably, the medicinal materials used before step (a) are pre-processing, wherein the medicinal materials are cut into decoction pieces with a size of about 0.5-1 cm;

55% of the prescription amount of *Poria cocos* decoction pieces are weighed for extraction;

the rest of the medicinal materials are all pure medicinal materials for use.

Further, the pre-processing also includes washing and drying the *Cortex moutan* in air, and then making the *Cortex moutan* into decoction pieces.

Preferably, in step (a), 45% of the prescription amount of the *Poria cocos* medicinal material is weighed to be dried and sterilized, and then pulverized into powder, and mixing well to obtain the *Poria cocos* powder intermediate;

Preferably, wherein

Sieving the powder obtained by pulverizing with a sieve of 60-200 meshes, preferably with a 120-mesh sieve.

Preferably, step (b) further includes the extraction of paeonol aromatic water, the refining of the *Cortex moutan* aromatic water, and the preparation of paeonol inclusion compound;

In the step of the extraction of the paeonol aromatic water, putting the decoction pieces of *Cortex moutan* into the extraction tank, and extracting the paeonol by steam distillation, filtering the paeonol by filter cloth, and collecting aromatic water in about 4-6 folds amount, preferably 5-fold amount; collecting medicinal dregs for use later; the filter cloth is of 80-200 meshes, preferably of 100 meshes.

In the step of the refining of the *Cortex moutan* aromatic water, resting the obtained paeonol aromatic water until the paeonol aromatic water is completely crystallized, and filtering the crystalsand then drying the crystals in the shade in a purifying zone to obtain paeonol crystals for use later; preferably, the filter cloth is of 80-200 meshes, preferably of 200 meshes.

In the step of the preparation of the paeonol inclusion compound, adding β-cyclodextrin to purified water in 2.7-fold amount of the β-cyclodextrin, stirring well, and heating; adding paeonol in an amount 1/6-1/12 of the addition of β-cyclodextrin to ethanol in 4-6 folds amount and heating paeonol to be dissolved; pouring the hot paeonol solution into the β-cyclodextrin solution and then processing the hot paeonol solution with a colloid mill and discharging; resting the solution overnight and then subjecting the solution by suction filtering, drying under normal pressure, pulverizing, and mixing to obtain the paeonol inclusion compound; preferably, sieving the addition of the paeonol is 1/10 of the addition of β-cyclodextrin, the addition of the ethanol is in 5-fold amount, the pulverized paeonol inclusion compound with a sieve of 60-200 meshes, preferably with a 100-mesh sieve; and the drying temperature under normal pressure is carried out at 40-90° C., preferably at 50° C.

Preferably, step (c) further includes the extraction of *Ramulus cinnamomi* aromatic water, the refining of the *Ramulus cinnamomi* aromatic water and the preparation of cinnamomi oil inclusion compound;

In the step of the extraction of the *Ramulus cinnamomi* aromatic water, putting the decoction pieces of *Ramulus cinnamomi* into the extraction tank and extracting the volatile oil by steam distillation; in the extraction process, adding the amount of ethyl acetate which is 3.5% of the amount of the medicinal material for extraction, and collecting the aromatic water at the ethyl acetate layer; preferably, the extraction time is 4-8 hours, preferably 5 hours;

In the step of the refining of *Ramulus cinnamomi* aromatic water, after resting the aromatic water at the ethyl acetate layer, separating the upper ethyl acetate layer is separated, re-extracting the lower layer with the same amount of ethyl acetate, combining the ethyl acetate layers and then concentrating, and adding ethanol in the same amount as the crude volatile oil for re-concentration to obtain pure volatile oil for use later; preferably, the concentration with ethyl acetate is carried out at 51-70° C., preferably at 60° C., and the concentration with ethanol is carried out at 70-95° C., preferably at 80° C.;

In the step of the preparation of the cinnamomi oil inclusion compound, adding β-cyclodextrin in 4-6 folds amount of ethanol, preferably in 5-fold amount, and stirring well to obtain a suspension; adding the volatile oil in an amount 1/6-1/12, preferably 1/10, of the addition of β-cyclodextrin to the suspension, stirring well, processing with a colloid mill and discharging; resting the solution overnight and subjecting by suction filtering, drying under normal pressure, pulverizing, and mixing to obtain the cinnamon oil inclusion compound; the ethanol is ethanol with a concentration of 10-50%, preferably of 20%; sieving the pulverized inclusion compound with a sieve of 60-200 meshes, preferably with a 100-mesh sieve; and the drying temperature under normal pressure is carried out at 40-90° C., preferably at 50° C.

Preferably, step (d) further includes extraction process, concentration, and spray drying steps; wherein, the extraction process further includes extraction on *Cortex moutan* dregs, extraction on *Ramulus cinnamomi* dregs, and extraction on *Radix paeoniae* alba, peach kernel and 55% of the prescription amount of *Poria cocos*; the concentration further includes the steps of alcohol extract concentration, water extract concentration, and combination and concentration; spray drying further includes: carrying out spray drying on the combined extract to obtain a spray-dried powder crude product, pulverizing and mixing the spray-dried powder crude product to obtain the spray-dried powder of the extract.

Further, in the step of extraction on *Cortex moutan* dregs, adding 90% ethanol for extraction in batches in a volume-weight ratio to the dregs obtained after extracting the aroma water from the *Cortex moutan*; filtering the extract is filtered, and combining the filtrate to obtain A1 for use later; the amount of ethanol added in batches is 3-5 folds first, preferably 4 folds, and then 2-4 folds, preferably 3 folds;

Water is further added for extraction in batches in a volume-weight ratio to the *Cortex moutan* dregs; the extract is filtered, and the filtrate is combined to obtain B1 for use later; discarding the extracted dregs; the amount of water added in batches is 5-8 folds first, preferably 6 folds, and then 2-6 folds, preferably 4 folds;

Preferably, the ethanol extraction is carried out for 1-4 times, preferably twice, the water extraction is carried out for 1-4 times, preferably twice, and each extraction with ethanol and water lasts for 2 hours.

Further, in the step of extraction on *Ramulus cinnamomi* dregs, adding 90% ethanol for extraction in batches in a volume-weight ratio to the dregs obtained after extracting the aroma water from the *Ramulus cinnamomi*; filtering the extract, and combining the filtrate is combined to obtain A2 for use later; the amount of ethanol added in batches is 3-5 folds first, preferably 4 folds, and then 2-4 folds, preferably 3 folds;

Further, adding water for extraction in batches in a volume-weight ratio to the *Ramulus cinnamomi* dregs; filtering the extract, and combining the filtrate to obtain B2 for use later; discarding the extracted dregs; the amount of water added in batches is 5-8 folds first, preferably 6 folds, and then 2-6 folds, preferably 4 folds;

Preferably, the ethanol extraction is carried out for 1-4 times, preferably twice, the water extraction is carried out for 1-4 times, preferably twice, and each extraction with ethanol and water lasts for 2 hours.

Further, in the step of extraction on *Radix paeoniae* alba, peach kernel and 55% of the prescription amount of *Poria cocos*, putting *Radix paeoniae* alba, peach kernel and 55% of the prescription amount of *Poria cocos* in the extraction tank, and adding 90% ethanol in batches in a volume-weight ratio of the medicinal materials; filtering the extract, and combining the filtrate to obtain A3 for use later; the amount of ethanol added in batches is 3-5 folds first, preferably 4 folds, and then 2-4 folds, preferably 3 folds;

Further, adding water for extraction in batches in a volume-weight ratio to the *Ramulus cinnamomi* dregs; filtering the extract, and combining the filtrate obtain B3 for use later; discarding the extracted dregs; the amount of water added in batches is 5-8 folds first, preferably 6 folds, and then 2-6 folds, preferably 4 folds.

Preferably, the *Radix paeoniae* alba, the peach kernel, and the *Poria cocos* are fed in an order of *Radix paeoniae* alba at the bottom, peach kernel in the middle, and *Poria cocos* at the top; the ethanol extraction is carried out for 1-4 times, preferably twice, the water extraction is carried out for 1-4 times, preferably twice, and each extraction with ethanol and water lasts for 2 hours.

Further, in the step of alcohol extract concentration, combining the alcohol extract liquids A1, A2, and A3, concentrating under reduced pressure to a relative density of 1.00-1.10, preferably 1.02-1.05, and weighting, obtaining an alcohol extract;

In the step of water extract concentration, combining the water extract liquids B1, B2, and B3, concentrating under reduced pressure to a relative density of 1.02-1.20, preferably 1.05-1.10, and weighting, obtaining a water extract;

In the step of combination and concentration, combining the concentrated liquid of the alcohol extract and the concentrated liquid of the water extract, further concentrating to a relative density of 1.05-1.30, preferably 1.15, and sieving with a sieve of 60-200 meshes, preferably a sieve of 80-100 meshes, to obtain an extract; refrigerating the obtained extract for storage or spray dried directly.

Further, in the step of spray drying the combined extract to obtain a crude spray-dried powder product, taking the combined extract for spray drying, and setting the inlet air temperature to 120-200° C., preferably 165-170° C., and controlling the outlet air temperature during the spray drying process to 80-110° C., preferably to 90-95° C.; cooling the crude spray-dried powder product to room temperature and then discharging, to obtain the spray dried powder;

In the step of pulverizing the crude spray-dried powder product, pulverizing all of obtained crude spray-dried powder product into the size of 60-200 meshes, preferably 100 meshes, to obtain the pulverized spray-dried powder.

Further, the total mixing is carried out for more than or equal to 5 minutes, preferably greater than or equal to 30 minutes, thus obtaining the final bulk drug.

The present invention further relates to a preparation method of a *Ramulus cinnamomi-Poria cocos* capsule, wherein the method comprises: dry granulating, sizing and well mixing the obtained bulk drug obtained in claim 14 to obtain granules, and filling the granules into capsule shells to obtain the finished product; preferably, sieving the dry granules with a sieve of 16-30 meshes, preferably of with a 24-mesh sieve.

Preferably, the method further includes the step of mixing the bulk drug with cyclodextrin.

The present invention further relates to a pharmaceutical composition comprising the composition of the present invention and a pharmaceutical carrier.

Further, wherein the composition is formulated into a preparation product, the preparation is in the form of pills, capsules, granules, tablets, suspensions or syrups.

The present invention further provides a medicine for treating or preventing primary dysmenorrhea, secondary dysmenorrhea, dysfunctional uterine bleeding, chronic pelvic inflammatory disease or small intramural uterine fibroids, wherein the medicine is made into a clinically acceptable dosage form by using any one of the foregoing compositions and a pharmaceutically acceptable excipient. These dosage forms can be decoctions, granules, capsules, tablets, oral liquids, pills, tinctures, suspensions, syrups, suppositories, gels, sprays, injections, etc.

Specifically, the preparation method of the capsule comprises: dry granulating, sizing and well mixing the composition or the bulk drug to obtain granules, controlling the moisture content of the granules within 5%, and filling the granules into capsule shells to obtain the finished product; preferably, sieving the dry granules with a 24-mesh sieve.

The present invention further provides an application of any of the foregoing compositions in the preparation of a medicine for treating or preventing any of the following diseases or conditions: primary dysmenorrhea, secondary dysmenorrhea, dysfunctional uterine bleeding, chronic pelvic inflammatory disease or small intramural uterine fibroids. Specifically, the application is that any of the foregoing compositions is administered orally, rectally, parenterally, intravaginally, intraperitoneally, topically, or as an oral or nasal spray.

The composition of the invention has a high content of effective ingredients, high production efficiency, high transfer rate of pchymic cid, reduced hygroscopicity, and improved dissolution of various index components. The preparation method has the following advantages:

(1) The process of drying, pulverizing, wet granulation and drying of the *Poria cocos* mixed extract is reduced, and the production efficiency is improved by more than 30%.

(2) The drying and pulverizing process of the *Poria cocos* mixed extract is reduced, and the transfer rate of pchymic cid is higher than 90%.

(3) During the process of making a preparation, since the *Poria cocos* powder is mixed with three other intermediates to be directly put in dry granulation, the moisture absorption rate of the product is obviously lower than the method used in the prior art by more than 60%.

(4) The content of each index component in the preparation is significantly higher than that in the preparation in the prior art process;

(5) Because the extract is directly spray dried and combined with other intermediates and then directly made into a preparation, the dissolution of each index component is significantly better than that of the method used in the prior art.

(6) The process rationality of the present invention after the improvement is obviously better than that of the prior art.

(7) Since the drying and pulverizing process of the *Poria cocos* mixed extract is reduced, the production intensity is low, the noise is low, and the dust production rate is low.

DETAILED DESCRIPTION OF PREFERRED EMBODIMENTS

The present invention discloses a composition containing Chinese herbal medicines *Ramulus cinnamomi* and *Poria cocos*, and a preparation method and application thereof. Those skilled in the art can learn from the content of the present disclosure to conduct the implementation by appropriately improving the process parameters. In particular, it should be pointed out that all similar substitutions and modifications obvious to those skilled in the art are all deemed to be included in the present invention.

Unless otherwise specified, the medicines, reagents, and instruments used in the technical solutions provided by the present invention can be purchased from conventional channels or markets.

Example 1 Preparation of a Capsule Comprising the Composition of the Present Invention

| 1. | Standard prescription of the capsule | |
| --- | --- | --- |
| | Ramulus cinnamomi | 360 g |
| | Poria cocos | 360 g |
| | Cortex moutan | 360 g |
| | Radix paeoniae alba | 360 g |
| | Peach kernel | 360 g |
| | prepared into 1000 granules (0.465 g/granule) | |
| 2. | Production prescription (400 prescription amount) | |
| | Ramulus cinnamomi | 144 kg |
| | Poria cocos | 144 kg |
| | Cortex moutan | 144 kg |
| | Radix paeoniae alba | 144 kg |
| | Peach kernel | 144 kg |
| | prepared into 400,000 granules (0.465 g/granule) | |
| 3. | Specific preparation method | |
| | Pre-processing | |
| | Pre-processing 1: | |

3. Specific Preparation Method
Pre-Processing
Pre-Processing 1:

The *Cortex moutan* in the above five herbs were rinsed with water for 2 minutes, dried in the air, and cut into decoction pieces of 0.5-1 cm in size for use later;

the rest of the medicinal materials were all pure medicinal materials for use; and 55% of the prescription amount of *Poria cocos* decoction pieces were weighed for extraction. Alternatively, Pre-Processing 2:

The above five herbs were all pure medicinal materials for use; and

55% of the prescription amount of *Poria cocos* decoction pieces are weighed for extraction.

(a) Preparation of *Poria cocos* Intermediate

A sufficient amount of *Poria cocos* powder was dried at 70° C. to a moisture content of ≤5.0% and then pulverized with a 120-mesh sieve; 30-49% of the prescription amount of *Poria cocos* powder was taken as the *Poria cocos* powder intermediate, wherein 45% of the prescription amount of *Poria cocos* was taken preferably.

(b) Preparation of Paeonol Inclusion Compound (1) Extraction of Paeonol Aromatic Water The *Cortex moutan* decoction pieces were put into a multifunctional extraction tank and subjected directly to steam distillation to extract paeonol. The filter cloth of about 100 meshes was used and the aromatic water in 5-fold amount (720 kg) was collected; the dregs were set aside for use later.

(2) Refining of the *Cortex moutan* Aromatic Water

The *Cortex moutan* aromatic water was allowed to rest for 48-72 hours until the aromatic water was completely crystallized; the crystals were filtered with a 200-mesh sieve, and then dried in the shade in the purifying zone to obtain 1.8-2.4 kg of paeonol crystals for use later.

(3) Paeonol Inclusion Compound

β-cyclodextrin was added to purified water in 2.7-fold amount of the β-cyclodextrin, stirred well, and heated to 60° C.; paeonol in an amount $1/10$ of the addition of β-cyclodextrin was added to 95% ethanol in 5-fold amount and then heated to be dissolved; the hot paeonol solution was poured into the β-cyclodextrin solution; the solution was processed with a colloid mill for 30 minutes and then discharged and allowed to rest overnight for 16-24 hours; the solution was subjected to suction filtering, drying at 50° C. under normal pressure, pulverizing into 100 meshes, and mixing to obtain 16.0-22.0 kg of the paeonol inclusion compound.

(c) Preparation of *Ramulus cinnamomi* Volatile Oil Inclusion Compound (1) Extraction of *Ramulus cinnamomi* Aromatic Water The decoction pieces of *Ramulus cinnamomi* were put into a multifunctional tank and subjected directly to steam distillation to extract volatile oil; in the extraction process, the amount of ethyl acetate which was 3.5% of the amount of the medicinal material was added for extraction, the extraction was carried out for 5 hours, and the aromatic water at the ethyl acetate layer was collected.

(2) Refining of *Ramulus cinnamomi* Aromatic Water

The aromatic water at the ethyl acetate layer was placed in a separating funnel and rested to separate the upper ethyl acetate layer, the lower layer was extracted with an equal amount of ethyl acetate, the ethyl acetate layers were combined and recovered at 60° C. under reduced pressure until there was no obvious droplet reflux; ethanol in an amount almost same as the crude volatile oil was added to the ethyl acetate layer, the solution was then concentrated at 80° C. until there was no obvious droplet reflux, and then concentrated at 90° C. for 20 minutes to obtain 0.50-0.90 L of pure volatile oil for use later.

(3) Cinnamomi Oil Inclusion Compound

β-cyclodextrin was added to 20% ethanol in 5-fold amount and stirred well to obtain suspension; Cinnamomi oil in an amount $1/10$ of the addition of β-cyclodextrin was added to the suspension, the solution was stirred well, processed with a colloid mill for 30 minutes and then discharged and allowed to rest for 16-24 hours; the solution was subjected to suction filtering, drying at 50° C. under normal pressure, pulverizing into 100 meshes, and mixing to obtain 5.0-9.0 kg of the Cinnamomi oil inclusion compound.

(d) Preparation of Spray-Dried Powder Intermediate of Extract (1) Extraction Process 1) Extraction on *Cortex moutan* Dregs 90% ethanol in 4+3 (volume-to-weight ratio, 576 L+432 L) folds amount was added to the *Cortex moutan* dregs left after extracting aromatic water from *Cortex moutan*, the extraction was carried out twice, 2 hours each time (working in the cycling mode for 5 minutes after boiling during each extraction), the extract liquid was filtered, and the filtrate was combined to obtain A1 for use later.

Water in 6+4 (864 L+576 L) folds amount was added to the *Cortex moutan* dregs, the extraction was carried out twice, 2 hours each time (working in the cycling mode for 5 minutes after boiling during each extraction), and the filtrate was combined to obtain B1 for use later; and the dregs were discarded.

2) Extraction on *Ramulus cinnamomi* Dregs

90% ethanol in 4+3 (volume-to-weight ratio, 576 L+432 L) folds amount was added to the *Ramulus cinnamomi* dregs left after extracting aromatic water from *Ramulus cinnamomi*, the extraction was carried out twice, 2 hours each time (working in the cycling mode for 5 minutes after boiling during each extraction), and the filtrate was combined to obtain A2 for use later.

Water in 6+4 (864 L+576 L) folds amount was added to the *Ramulus cinnamomi* dregs, the extraction was carried out twice, 2 hours each time (working in the cycling mode for 5 minutes after boiling during each extraction), and the filtrate was combined to obtain B2 for use later; and the dregs were discarded.

3) Extraction on *Radix paeoniae* Alba, Peach Kernel and 55% of the Prescription Amount of *Poria cocos*

*Radix paeoniae* alba, peach kernel, and 55% of the prescription amount of *Poria cocos* were fed in an order of *Radix paeoniae* alba at the bottom, peach kernel in the middle, and *Poria cocos* at the top; 90% ethanol as 4+3 (volume-to-weight ratio, 1468.8 L+1101.6 L) folds as the amount of the medicinal materials was added to perform extraction twice, 2 hours each time (working in the cycling mode for 5 minutes after boiling during each extraction), and the filtrate was combined to obtain A3 for use later.

Water in 6+4 (2203.2 L+1468.8 L) folds amount was added to the dregs, the extraction was carried out twice, 2 hours each time (working in the cycling mode for 5 minutes after boiling during each extraction), and the filtrate was combined to obtain B3 for use later; and the dregs were discarded.

(2) Concentration

1) Concentration of Alcohol Extract Liquid

The alcohol extract liquids A1, A2, and A3 were combined and concentrated under reduced pressure. The alcohol extract liquid was recovered to a relative density of 1.02-1.05 (70±5° C.) and weighed to obtain the alcohol extract.

2) Concentration of Water Extract Liquid

The water extract liquids B1, B2, and B3 were combined, and concentrated under reduced pressure to a relative density of 1.05-1.10 (80±5° C.), weighted to obtain a water extract.

3) Combination and Concentration

The concentrated liquid of the alcohol extract and the concentrated liquid of the water extract were combined, further concentrated to a relative density of 1.15 (80±5° C.), and sieved with a sieve of 80-100 meshes to obtain an extract; the obtained extract was refrigerated for storage or spray dried directly.

(3) Spray Drying Process

1) Spray Drying

The combined extract was spry dried, the inlet air temperature was set to 165-170° C., and the outlet air temperature was controlled to 90-95° C. during the spray-drying process; the resulting powder was cooled to room temperature, and then discharged, thus obtaining the spray-dried powder.

2) Mixing of Spray-Dried Powder

The pulverized spry-dried powder was mixed for a time ≥15 minutes, and the spry-dried powder of the extract was finally obtained for use later.

(e) Total Mixing

The *Poria cocos*, the spray-dried powder, the paeonol inclusion compound, and Cinnamomi oil inclusion compound were mixed together for total mixing for a time ≥30 minutes to obtain the final bulk drug.

(f) Preparation

The bulk drug was dry-granulated (24 meshes), sized, well mixed to obtain granules, 0.465 g/granule; the granules were filled into No. 0 green capsule shells to obtain the finished product.

4. Comparison of the Preparation Method of the Present Invention with the Method Disclosed in the Prior Art CN200780027994.4

TABLE 1

Comparison of production efficiency

| Different processes | Time of process step | | | | | | | |
|---|---|---|---|---|---|---|---|---|
| | Pulverizing of Poria cocos | Extraction | Concentration | Drying process | Pulverizing | Inclusion | Granulation | Total (h) |
| Prior art | 8 h | 12 h | 8 h | Poria cocos powder was mixed with the extract and dried under normal pressure for 20 hours | 10 h | 24 h | (Soft material powder + 2 inclusion compounds) wet granulation and drying, the sizing process time was 16 hours | 98 h |
| The method of the present invention | 5 h | 12 h | 8.5 h | The extract was directly spray dried for 8 hours | — | 24 h | (Extract powder + 2 inclusion compounds + Poria cocos powder) dry granulation time was 10 hours | 67.5 h |
| Improvement | −3 | 0 | 0.5 | −12 | −10 | 0 | −6 | −30.5 h |

It can be seen from Table 1 that the combined extract of the present invention is directly spray-dried to obtain medicinal powder, and the paeonol inclusion compound, *Ramulus cinnamomi* volatile oil inclusion compound, and *Poria cocos* powder are directly combined for dry granulation. Compared with the prior art, the present invention reduces the process of drying, pulverizing, wet granulating drying of the *Poria cocos* mixed extract. The production efficiency of the preparation method in the present invention is improved by 30% or above.

TABLE 2

Comparison of the content of each index component

| Different processes | Indicator component (mg/g) | | | | | |
|---|---|---|---|---|---|---|
| | Paeoniflorin | Amygdalin | Benzoyl-paeoniflorin | Cinnamic acid | Paeonol | Cinnamaldehyde |
| Prior art | 11.29 | 3.87 | — | — | 6.45 | — |
| The method of the present invention (Batch 1) | 18.98 | 15.00 | 0.85 | 1.21 | 12.23 | 2.12 |

TABLE 2-continued

Comparison of the content of each index component

| Different processes | Indicator component (mg/g) | | | | | |
|---|---|---|---|---|---|---|
| | Paeoniflorin | Amygdalin | Benzoyl-paeoniflorin | Cinnamic acid | Paeonol | Cinnamaldehyde |
| The method of the present invention (Batch 2) | 15.26 | 13.22 | 0.80 | 1.09 | 11.16 | 2.02 |
| The method of the present invention (Batch 3) | 17.33 | 14.04 | 0.91 | 1.25 | 12.01 | 2.25 |
| Improvement | Compared with the prior art, the present invention is significantly improved in the contents of the index components | | | | | |

It can be determined from the data in Table 2 that in the preparation of the present invention, the effective ingredients are significantly increased, and the content of each index component is significantly higher than that in the prior art.

TABLE 3

Comparison of transfer rate of poriaic acid

| Different processes | Transfer rate % of poriaic acid | | |
|---|---|---|---|
| | Batch 1 | Batch 2 | Batch 3 |
| Prior art | 60.2 | 57.8 | 58.4 |
| The method of the present invention | 90.6 | 91.3 | 92.5 |
| Improvement | Compared with the prior art process, the present process reduces the process of drying, pulverizing, wet granulating drying of the Poria cocos mixed | | |

TABLE 4

Comparison of products in moisture absorption rate

| Different processes | Moisture absorption percentage % | | |
|---|---|---|---|
| | Sample 1 | Sample 2 | Sample 3 |
| Prior art | 3.25 | 3.04 | 3.16 |
| The method of the present invention | 1.25 | 1.08 | 1.21 |
| Improvement | The Moisture absorption rate is obviously lower than that the prior art process | | |

From the data in Table 4, it can be determined that in the present invention, since the *Poria cocos* powder is mixed with three other intermediates during the process of making a preparation to be directly put in dry granulation (no added solvent), the moisture absorption rate of the product is obviously lower than the method used in the prior art by more than 60%.

TABLE 5

Comparison in the dissolution of each index component in the preparation

| Different processes | Dissolution % | | | | | |
|---|---|---|---|---|---|---|
| | Paeoniflorin | Amygdalin | Benzoyl-paeoniflorin | Cinnamic acid | Paeonol | Cinnamaldehyde |
| Prior art | 62.5 | 59.7 | 56.3 | 59.6 | 62.4 | 56.4 |
| The method of the present invention | 89.6 | 86.5 | 88.4 | 84.8 | 87.8 | 90.4 |
| Improvement | Compared with the prior art process, the present invention is significantly improved in the dissolution of the index components | | | | | |

TABLE 3-continued

Comparison of transfer rate of poriaic acid

| Different processes | Transfer rate % of poriaic acid | | |
|---|---|---|---|
| | Batch 1 | Batch 2 | Batch 3 |
| | extract, so the transfer rate of poriaic acid is significantly improved. | | |

It can be determined from the data in Table 3 that the present invention reduces the process of drying, pulverizing, wet granulating drying of the *Poria cocos* mixed extract, and the transfer rate of poriaic acid reaches 90% or above, which is much higher than the transfer rate of poriaic acid in the method used in the prior art.

It can be determined from the data in Table 5 that in the present invention, because the extract is directly spray dried and combined with other intermediates and then directly made into a preparation, the dissolution of each index component is significantly better than that of the method used in the prior art.

TABLE 6

Comparison in rationality of preparation process

| Different processes | Comparison in advantage and disadvantage | | |
|---|---|---|---|
| | Drying | Pulverizing | Granulation drying |
| Method of the prior art | The extract is mixed with Poria cocos powder | The pulverizing process of the dried soft material | Wet granulation takes a long time, has high energy |

TABLE 6-continued

Comparison in rationality of preparation process

| Different processes | Comparison in advantage and disadvantage | | |
|---|---|---|---|
| | Drying | Pulverizing | Granulation drying |
| | and dried: it takes a long time, the operation technology is backward, the labor intensity is high, and it is likely to cause pollution. | powder causes high noise, high dust production rate and environmental pollution. | consumption and high intensity, and is likely to cause pollution. |
| Method of the present invention | Direct spray drying of the extract: it takes a short time, and has advanced technology, low labor intensity and no pollution. | The fine powder of the medicine can be obtained directly through spray drying without pulverizing. | Low time cost, low energy consumption, low intensity, and no pollution. |
| Improvement | The process and operation method are relatively reasonable. | | |

It can be determined from Table 6 that the rationality of the preparation process of the present invention is obviously better than that of the method used in the prior art.

It can be seen that the active ingredient content, dissolution rate, moisture absorption rate, the pachymic acid transfer rate, production efficiency, etc., and various process parameters of the composition of the present invention are significantly better than those in the prior art.

It should be noted that those skilled in the art can learn from the content of the present disclosure to conduct the implementation by appropriately improving the process parameters. All similar replacements and modifications obvious to those skilled in the art are considered to be included in the present invention.

What is claimed is:

1. A method for preparing a traditional Chinese medicine composition comprising *Ramulus cinnamomi*, *Poria cocos*, *Cortex moutan*, *Radix paeoniae* alba, and peach kernel in equal proportions, comprising following steps:
    (a) preparation of a *Poria cocos* powder intermediate: pulverizing 30-49% of the *Poria cocos* to obtain the *Poria cocos* powder intermediate;
    (b) preparation of a paeonol inclusion compound: extracting paeonol from *Cortex moutan* by direct connection steam distillation, and collecting aromatic water and medicinal dregs for use later; resting the aromatic water for 48-72 hours until crystals are completely crystallized, and filtering and drying in shade to obtain paeonol crystals; and including with β-cyclodextrin to prepare a paeonol inclusion compound;
    (c) preparation of a *Ramulus cinnamomi* volatile oil inclusion compound: extracting volatile oil from *Ramulus cinnamomi* by direct connection steam distillation, adding ethyl acetate during the extracting process, and collecting aromatic water from ethyl acetate layers and medicinal dregs for use later; placing the aromatic water in a separating funnel, resting the aromatic water, separating an upper ethyl acetate layer, extracting a lower layer with equal amount of ethyl acetate, combining the ethyl acetate layers, carrying out reduced-pressure recovery, and adding ethanol for further concentration to obtain pure volatile oil; including with β-cyclodextrin to prepare the *Ramulus cinnamomi* volatile oil inclusion compound;
    (d) preparation of spray-dried powder intermediates of extracts: carrying out alcohol extraction and water extraction on *Cortex moutan* dregs, carrying out alcohol extraction and water extraction on *Ramulus cinnamomi* dregs, and carrying out alcohol extraction and water extraction on *Radix paeoniae* alba, peach kernel, and 51-70% of the *Poria cocos*; concentrating the alcohol extracts or water extracts separately, combining the concentrated extracts for further concentration to obtain extract, and mixing after spray drying to obtain spray-dried powder; and
    (e) total mixing: mixing the *Poria cocos* powder intermediate, the spray-dried powder intermediates of extracts, the paeonol inclusion compound, and the *Ramulus cinnamomi* volatile oil inclusion compound to obtain the traditional Chinese medicine composition.

2. The method according to claim 1, wherein in step (a), drying the *Poria cocos* at 70° C. to the moisture content of ≤5.0%, then pulverizing the *Poria cocos* with a 120-mesh sieve, and taking 45% of the *Poria cocos* powder.

3. The method according to claim 1, wherein step (b) comprises:
    collecting the aromatic water in a fourfold to sixfold amount of the *Cortex moutan* during the steam distillation process;
    including with β-cyclodextrin specifically comprises: adding β-cyclodextrin to purified water in a 2.7-fold amount of the β-cyclodextrin, stirring well, and heating to 60° C. to obtain a β-cyclodextrin solution; adding paeonol in a ⅙-1/12 amount of the addition of β-cyclodextrin to ethanol in a fourfold to sixfold amount thereof and then heating to dissolve the paeonol; pouring the hot paeonol solution into the β-cyclodextrin solution; processing the solution with a colloid mill for 30 minutes and then discharging the solution, and resting for 16-24 hours; carrying out by suction filtering, drying at 50° C., pulverizing with a 100-mesh sieve, and mixing to obtain the paeonol inclusion compound.

4. The method according to claim 1, wherein step (c) comprises:
    adding ethyl acetate during the steam distillation process in 3.5% amount of the *Ramulus cinnamom*;
    including with β-cyclodextrin specifically comprises: adding β-cyclodextrin to ethanol in a fourfold to sixfold amount thereof, and stirring well to obtain a suspension; adding the volatile oil in a ⅙-1/12 amount of the addition of β-cyclodextrin to the suspension, stirring well, processing the solution with a colloid mill for 30 minutes, discharging the solution, resting for 16-24 hours, carrying out by suction filtering, drying at 50° C., pulverizing with a 100-mesh sieve, and mixing to obtain the *Ramulus cinnamomi* volatile oil inclusion compound.

5. The method according to claim 1, wherein step (d) comprises:
    feeding the *Radix paeoniae* alba, the peach kernel, and the 51-70% of the *Poria cocos* in an order of *Radix paeoniae* alba at the bottom, peach kernel in the middle, and *Poria cocos* at the top.

6. A traditional Chinese medicine composition prepared by the method according to claim 1, comprising *Ramulus cinnamomi*, *Poria cocos*, *Cortex moutan*, *Radix paeoniae* alba, and peach kernel in equal proportions, wherein the traditional Chinese medicine composition further contains paeoniflorin, amygdalin, benzoylpaeoniflorin, cinnamic acid, paeonol, and cinnamic aldehyde, wherein the content of Paeoniflorin accounts for 15 mg/g or above of the traditional Chinese medicine composition, the content of amygdalin accounts for 10 mg/g or above of the traditional Chinese medicine composition, and the content of Paeonol accounts for 10 mg/g or above of the traditional Chinese medicine composition.

7. The traditional Chinese medicine composition according to claim 6, wherein a transfer rate of Pachymic acid from *Poria cocos* to the traditional Chinese medicine composition is greater than 90%.

8. A medicine, made into a clinically acceptable dosage form, comprising the composition according to claim 6 and a pharmaceutically acceptable excipient.

9. A method of treating or preventing any of the following diseases or conditions: primary dysmenorrhea, secondary dysmenorrhea, dysfunctional uterine bleeding, chronic pelvic inflammatory disease and small intramural uterine fibroids, comprising administering the composition according to claim 6 to a subject in need thereof.

10. The method according to claim 4 wherein the volatile oil is added in a $\frac{1}{10}$ amount of the addition of β-cyclodextrin to the suspension.

\* \* \* \* \*